United States Patent
Monello

(10) Patent No.: US 8,980,234 B2
(45) Date of Patent: Mar. 17, 2015

(54) COSMETIC COMPOSITION COMPRISING AN ASCORBIC ACID OR SALICYLIC ACID COMPOUND

(75) Inventor: Aldo Monello, Savigny sur Orge (FR)

(73) Assignee: L'Oreal, Paris (FR)

( * ) Notice: Subject to any disclaimer, the term of this patent is extended or adjusted under 35 U.S.C. 154(b) by 704 days.

(21) Appl. No.: 12/400,178

(22) Filed: Mar. 9, 2009

(65) Prior Publication Data

US 2009/0232756 A1 Sep. 17, 2009

Related U.S. Application Data

(60) Provisional application No. 61/037,002, filed on Mar. 17, 2008, provisional application No. 61/037,001, filed on Mar. 17, 2008.

(30) Foreign Application Priority Data

Mar. 11, 2008 (FR) ...................................... 08 51555
Mar. 11, 2008 (FR) ...................................... 08 51556

(51) Int. Cl.
| | | |
|---|---|---|
| A61K 8/00 | (2006.01) |
| A61Q 17/04 | (2006.01) |
| A01N 37/36 | (2006.01) |
| A61K 31/60 | (2006.01) |
| A01N 43/08 | (2006.01) |
| A61K 31/34 | (2006.01) |
| A61K 8/02 | (2006.01) |
| A61K 8/30 | (2006.01) |
| A61K 8/67 | (2006.01) |
| A61K 8/368 | (2006.01) |
| A61K 8/37 | (2006.01) |
| A61K 8/49 | (2006.01) |
| A61K 8/86 | (2006.01) |
| A61K 8/90 | (2006.01) |
| A61Q 19/00 | (2006.01) |

(52) U.S. Cl.
CPC ................ *A61K 8/676* (2013.01); *A61K 8/368* (2013.01); *A61K 8/375* (2013.01); *A61K 8/4993* (2013.01); *A61K 8/86* (2013.01); *A61K 8/90* (2013.01); *A61Q 19/00* (2013.01)
USPC .......... 424/60; 424/401; 424/70.31; 514/159; 514/474

(58) Field of Classification Search
USPC .................. 424/60, 401, 70.31; 514/159, 474
See application file for complete search history.

(56) References Cited

U.S. PATENT DOCUMENTS

| | | | | |
|---|---|---|---|---|
| 5,976,555 | A | * | 11/1999 | Liu et al. ........................ 424/401 |
| 6,309,663 | B1 | * | 10/2001 | Patel et al. .................... 424/450 |
| 6,696,070 | B2 | * | 2/2004 | Dunn ............................. 424/402 |
| 2004/0047885 | A1 | * | 3/2004 | Cupferman et al. .......... 424/401 |
| 2004/0166128 | A1 | | 8/2004 | Noel et al. |
| 2005/0220831 | A1 | * | 10/2005 | Jorsal ............................ 424/401 |
| 2006/0147396 | A1 | | 7/2006 | Monello |
| 2007/0098655 | A1 | * | 5/2007 | Schmaus et al. ................ 424/62 |
| 2007/0269390 | A1 | | 11/2007 | Inoue |
| 2011/0052512 | A1 | * | 3/2011 | Monello et al. ................. 424/59 |

FOREIGN PATENT DOCUMENTS

| | | |
|---|---|---|
| DE | 199 35 763 | 2/2001 |
| DE | 103 56 895 | 4/2005 |
| EP | 1 415 645 | 5/2004 |
| EP | 1 676 563 | 7/2006 |
| FR | 2 585 575 | 2/1987 |
| JP | 2004-508318 | 3/2004 |
| JP | 2006-188517 | 7/2006 |
| WO | 02/19984 A2 | 3/2002 |
| WO | WO 02/19984 | 3/2002 |
| WO | WO 2004105736 A1 * | 12/2004 |
| WO | WO 2006/102004 | 9/2006 |

OTHER PUBLICATIONS

Office Action issued Aug. 13, 2013, in JP Application No. 2009-056470 with English translation.
Japanese Office Action issued Mar. 25, 2014 in Patent Application No. 2009-056470 (English Translation only).

* cited by examiner

*Primary Examiner* — Abigail Fisher
(74) *Attorney, Agent, or Firm* — Oblon, McClelland, Maier & Neustadt, L.L.P.

(57) ABSTRACT

A composition in the form of an oil-in-water emulsion containing:
  an ester of fatty acid and of polyethylene glycol;
  an additional surfactant chosen from esters of $C_{16}$-$C_{22}$ fatty acid and of sorbitan and esters of $C_{16}$-$C_{22}$ fatty acid and of glycerol;
  a polycondensate of ethylene oxide and of propylene oxide consisting of polyethylene glycol and polypropylene glycol blocks; and
  an ascorbic acid compound or a salicylic acid compound.
The composition has good stability, in particular after hours at 55° C. Application in caring for and making up keratinous substances.

19 Claims, No Drawings

COSMETIC COMPOSITION COMPRISING AN ASCORBIC ACID OR SALICYLIC ACID COMPOUND

REFERENCE TO PRIOR APPLICATIONS

This application claims priority to U.S. provisional application Nos. 61/037,001 and 61/037,002, both filed Mar. 17, 2008; and to French patent application Nos. 0851555 and 0851556, both filed Mar. 11, 2008, both incorporated herein by reference.

FIELD OF THE INVENTION

A subject-matter of the present invention is an oil-in-water emulsion comprising at least one active principle chosen from an ascorbic acid compound and a salicylic acid compound, and a specific surfactant mixture.

BACKGROUND

Ascorbic acid or vitamin C and its derivatives are commonly used as a result of their many beneficial properties. In particular, ascorbic acid stimulates the synthesis of the connective tissue and in particular of collagen, strengthens the defenses of the cutaneous tissue against external attacks, such as ultraviolet radiation and pollution, compensates for vitamin E deficiency of the skin, depigments the skin and has a role in combating free radicals. These last two properties make it an excellent candidate as cosmetic or dermatological active principle for combating ageing of the skin or for preventing ageing of the skin. Unfortunately, because of its chemical structure (of alpha-ketolactone), ascorbic acid is highly sensitive to certain environmental parameters and in particular to oxidation phenomena. There thus ensues rapid decomposition of formulated ascorbic acid in the presence of these parameters and more particularly in the presence of oxygen, light or metal ions, as a function of the temperature or under certain pH conditions (Pharm. Acta. Helv., 1969, 44, 611-667; STP Pharma, 1985, 4, 281-286).

Furthermore, it is known to use salicylic acid and its derivatives in topical compositions, in particular cosmetic or dermatological topical compositions, for example as keratolytic agent for treating acne or as antiageing agent. The documents FR-A-2 581 542 and EP-A-378 936 describe such derivatives.

However, the use of ascorbic acid or salicylic acid or their derivatives in emulsions, in particular in oil-in-water emulsions, especially when they comprise a surfactant system comprising an ester of fatty acid and of polyethylene glycol, and an additional surfactant chosen from esters of $C_{16}$-$C_{22}$ fatty acid and of sorbitan and esters of $C_{16}$-$C_{22}$ fatty acid and of glycerol, has a tendency to destabilize the emulsion, which then exhibits a phase separation of oil at the surface. The oil globules dispersed in the aqueous phase have a coarse appearance, rendering the emulsion nonhomogeneous.

In point of fact, this surfactant system described above is advantageous for the specific texture which it confers on these emulsions. The latter have a thick texture and are suitable for packaging of the cosmetic product in a pot (in contrast to fluid textures, which are packaged in a tube or in a pump-action spray; the thick texture is such that the composition does not flow instantaneously on turning the pot upside down); such a composition can be easily taken up with the fingers and spreads well and pleasantly over the skin while readily penetrating it; it confers softness and does not exhibit a tacky effect.

SUMMARY OF THE INVENTION

The aim of the present invention is thus to make available an emulsion comprising an active principle chosen from ascorbic acid, salicylic acid or one of their derivatives and the surfactant system described above which is stable, in particular for 24 hours at 55° C., indeed even for 2 months at 45° C.

The inventor has discovered that the stability of such an emulsion can be obtained by adding a polycondensate of ethylene oxide and of propylene oxide.

More specifically, a subject-matter of the invention is a composition in the form of an oil-in-water emulsion comprising:
one or more of an ascorbic acid compound and/or a salicylic acid compound;
an ester of fatty acid and of polyethylene glycol;
one or more additional surfactants chosen from esters of $C_{16}$-$C_{22}$ fatty acid and of sorbitan and esters of $C_{16}$-$C_{22}$ fatty acid and of glycerol, this/these additional surfactant(s) being different from the above ester of fatty acid and of polyethylene glycol;
a polycondensate of ethylene oxide and of propylene oxide.

DETAILED DESCRIPTION OF THE PREFERRED EMBODIMENTS

The embodiments of the invention can all include multiple species of a listed genus or subgenus. This is often indicated by the term "at least one of", "and mixtures thereof", etc., but these terms need not be present to denote the inclusion of multiple species of a given type in the invention compositions.

According to a first embodiment, a subject-matter of the invention is a composition in the form of an oil-in-water emulsion comprising:
an ascorbic acid compound;
an ester of fatty acid and of polyethylene glycol;
an additional surfactant chosen from esters of $C_{16}$-$C_{22}$ fatty acid and of sorbitan and esters of $C_{16}$-$C_{22}$ fatty acid and of glycerol;
a polycondensate of ethylene oxide and of propylene oxide.

As noted above, and repeated here to emphasize the point, the above description of the first embodiment includes multiple ascorbic acid compounds, etc.

According to a second embodiment, a subject-matter of the invention is a composition in the form of an oil-in-water emulsion comprising:
a salicylic acid compound;
an ester of fatty acid and of polyethylene glycol;
an additional surfactant chosen from esters of $C_{16}$-$C_{22}$ fatty acid and of sorbitan and esters of $C_{16}$-$C_{22}$ fatty acid and of glycerol;
a polycondensate of ethylene oxide and of propylene oxide.

Another subject-matter of the invention is a non-therapeutic method for caring for or making up keratinous substances, comprising the application, to the keratinous substances, of the composition defined above.

The ascorbic acid compound present in the composition according to the invention is advantageously chosen from ascorbic acid and its salts, such as magnesium ascorbyl phosphate or sodium ascorbyl phosphate, and also glycosyl ascorbic acid, and their mixtures.

The ascorbic acid compound is preferably chosen from magnesium ascorbyl phosphate and glycosyl ascorbic acid, and their mixture.

The ascorbic acid compound as described above can be present in the emulsion according to the invention in a content ranging for example from 0.05% to 10% by weight, with respect to the total weight of the composition, preferably ranging from 0.05% to 5% by weight and preferentially ranging from 0.1% to 3% by weight.

The salicylic acid compound present in the composition according to the invention is advantageously chosen from salicylic acid and the compounds of following formula (I):

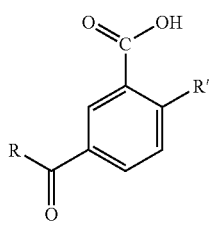

(I)

in which:
the R radical denotes a saturated, linear, branched or cyclic, aliphatic chain having from 2 to 22 carbon atoms; an unsaturated chain having from 2 to 22 carbon atoms comprising one or more double bonds which can be conjugated; an aromatic nucleus bonded to the carbonyl radical directly or via saturated or unsaturated aliphatic chains having from 2 to 7 carbon atoms; it being possible for the said groups to be substituted by one or more identical or different substituents chosen from (a) halogen atoms, (b) the trifluoromethyl group, (c) hydroxyl groups in the free form or in the form esterified by an acid having from 1 to 6 carbon atoms or (d) a carboxyl functional group in the free form or in the form esterified by a lower alcohol having from 1 to 6 carbon atoms;
R' is a hydroxyl group;
and their salts resulting from an inorganic or organic base.

Preferably, the R radical denotes a saturated, linear, branched or cyclic, aliphatic chain comprising from 3 to 11 carbon atoms; an unsaturated chain comprising from 3 to 17 carbon atoms and comprising one or more conjugated or nonconjugated double bonds; it being possible for the said hydrocarbon chains to be substituted by one or more identical or different substituents chosen from (a) halogen atoms, (b) the trifluoromethyl group, (c) hydroxyl groups in the free form or in the form esterified by an acid having from 1 to 6 carbon atoms or (d) a carboxyl functional group in the free form or in the form esterified by a lower alcohol having from 1 to 6 carbon atoms;
and their salts obtained by salification by an inorganic or organic base.

The compounds more particularly preferred are those in which the R radical is a $C_3$-$C_{11}$ alkyl group.

Mention may be made, among the compounds of formula (I) which are particularly preferred, of: 5-(n-octanoyl)salicylic acid (or caproyloxysalicylic acid); 5-(n-decanoyl)salicylic acid; 5-(n-dodecanoyl)-salicylic acid; 5-(n-heptyloxy) salicylic acid and their corresponding salts.

The salicylic acid compound is advantageously chosen from salicylic acid and 5-(n-octanoyl)salicylic acid. Use is more particularly made of 5-(n-octanoyl)salicylic acid.

The salts of the compounds of formula (I) can be obtained by salification by an inorganic or organic base. Mention may be made, as examples of inorganic base, of alkali metal or alkaline earth metal hydroxides, such as sodium hydroxide or potassium hydroxide, or ammonia.

Mention may be made, among organic bases, of amines and alkanolamines. Quaternary salts, such as those described in Patent FR 2 607 498, are particularly advantageous.

The compounds of formula (I) which can be used according to the invention are described in U.S. Pat. No. 6,159,479 and U.S. Pat. No. 5,558,871, FR 2 581 542, FR 2 607 498, U.S. Pat. No. 4,767,750, EP 378 936, U.S. Pat. No. 5,267,407, U.S. Pat. No. 5,667,789, U.S. Pat. No. 5,580,549 and EP-A-570 230.

The salicylic acid compound as described above can be present in the emulsion according to the invention in a content ranging for example from 0.05% to 10% by weight, with respect to the total weight of the composition, preferably ranging from 0.05% to 5% by weight and preferentially ranging from 0.1% to 3% by weight.

The composition according to the invention comprises, as main emulsifying surfactant, at least one ester of fatty acid and of polyethylene glycol.

The ester of fatty acid and of polyethylene glycol present in the composition according to the invention is preferably a $C_{16}$-$C_{22}$ fatty acid ester comprising from 8 to 100 ethylene oxide units.

The fatty chain of the esters can be chosen in particular from stearyl, behenyl, arachidyl, palmityl or cetyl units and their mixtures, such as cetearyl, and preferably a stearyl chain.

The number of ethylene oxide units can range from 8 to 100, preferably from 10 to 80 and better still from 10 to 50. According to a specific embodiment of the invention, this number can range from 20 to 40.

Mention may be made, as examples of ester of fatty acid and of polyethylene glycol, of stearic acid esters respectively comprising 20, 30, 40, 50 or 100 ethylene oxide units, such as the products respectively sold under the names Myrj 49 P (polyethylene glycol 20 EO stearate; CTFA name: PEG-20 stearate), Myrj 51, Myrj 52 P (polyethylene glycol 40 EO stearate; CTFA name: PEG-40 stearate), Myrj 53 and Myrj 59 P by Croda.

The ester of fatty acid and of polyethylene glycol can be present in the composition according to the invention in a content ranging from 0.1% to 10% by weight, with respect to the total weight of the composition, preferably ranging from 0.1% to 5% by weight and preferentially ranging from 0.1% to 3% by weight.

The composition according to the invention also comprises an additional emulsifying surfactant chosen from esters of $C_{16}$-$C_{22}$ fatty acid and of sorbitan and esters of $C_{16}$-$C_{22}$ fatty acid and of glycerol.

According to a first embodiment of the invention, the composition comprises an ester of $C_{16}$-$C_{22}$ fatty acid and of sorbitan.

The esters of $C_{16}$-$C_{22}$ fatty acid and of sorbitan are formed by esterification, with sorbitol, of at least one fatty acid comprising at least one saturated or unsaturated linear alkyl chain respectively having from 16 to 22 carbon atoms. These esters can be chosen in particular from sorbitan stearates, behenates, arachidates, palmitates or oleates, and their mixtures. Use is preferably made of sorbitan stearates and palmitates and preferentially sorbitan stearates.

The ester of $C_{16}$-$C_{22}$ fatty acid and of sorbitan present in the composition according to the invention is advantageously solid at a temperature of less than or equal to 45° C.

Mention may be made, as examples of sorbitan ester which can be used in the composition according to the invention, of the sorbitan monostearate (CTFA name: Sorbitan stearate) sold by Croda under the name Span 60, the sorbitan tristearate sold by Croda under the name Span 65 V, the sorbitan monopalmitate (CTFA name: Sorbitan palmitate) sold by Croda under the name Span 40, the sorbitan monooleate sold by Croda under the name Span 80 V or the sorbitan trioleate sold by Uniqema under the name Span 85 V. Preferably, the sorbitan ester used is sorbitan tristearate.

The ester of $C_{16}$-$C_{22}$ fatty acid and of sorbitan may be present in the composition according to the invention in a content ranging for example from 0.01% to 10% by weight, with respect to the total weight of the composition, preferably ranging from 0.01% to 5% by weight and preferentially ranging from 0.1% to 3% by weight.

The ester of glycerol and of fatty acid can be obtained in particular from an acid comprising a saturated linear alkyl chain having from 16 to 22 carbon atoms. Mention may in particular be made, as ester of glycerol and of fatty acid, of glyceryl stearate (glyceryl mono-di- and/or tristearate) (CTFA name: Glyceryl stearate), glyceryl ricinoleate and their mixtures. Preferably, the ester of glycerol and of fatty acid used is chosen from glyceryl stearates.

The ester of glycerol and of fatty acid can be present in an amount ranging for example from 0.1% to 10% by weight, with respect to the total weight of the composition, preferably ranging from 0.1% to 5% by weight and preferentially ranging from 0.1% to 3% by weight.

The composition of the invention can in particular be a mixture of glyceryl stearate and of polyethylene glycol 100 EO monostearate and in particular that comprising a 50/50 mixture sold under the name Arlacel 165 by Croda.

The composition according to the invention comprises a polycondensate of ethylene oxide and of propylene oxide and more particularly a copolymer consisting of polyethylene glycol and polypropylene glycol blocks, such as, for example, polyethylene glycol/polypropylene glycol/polyethylene glycol triblock polycondensates. These triblock polycondensates have, for example, the following chemical structure:

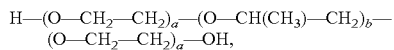

in which formula a ranges from 2 to 150 and b ranges from 1 to 100; preferably, a ranges from 10 to 130 and b ranges from 20 to 80.

The polycondensate of ethylene oxide and of propylene oxide preferably has a weight-average molecular weight ranging from 1000 to 15,000, better still ranging from 1500 to 15,000, in particular ranging from 1500 to 10,000 and even better still ranging from 1500 to 5000.

Advantageously, the said polycondensate of ethylene oxide and of propylene oxide has a cloud temperature, at 10 g/l in distilled water, of greater than or equal to 20° C., preferably of greater than or equal to 60° C. The cloud temperature is measured according to Standard ISO 1065.

Mention may be made, as polycondensate of ethylene oxide and of propylene oxide which can be used according to the invention, of the polyethylene glycol/polypropylene glycol/polyethylene glycol triblock polycondensates sold under the "Synperonic" names, such as "Synperonic® PE/F32" (INCI name: Poloxamer 108), "Synperonic® PE/F108" (INCI name: Poloxamer 338), "Synperonic® PE/L44" (INCI name: Poloxamer 124), "Synperonic® PE/L42" (INCI name: Poloxamer 122), "Synperonic® PE/F127" (INCI name: Poloxamer 407), "Synperonic® PE/F88" (INCI name: Poloxamer 238) or "Synperonic® PE/L64" (INCI name: Poloxamer 184), by Croda or also "Lutrol® F68" (INCI name: Poloxamer 188), sold by BASF.

The polycondensate of ethylene oxide and of propylene oxide can be present in the composition according to the invention in a content ranging for example from 0.01% to 5% by weight, with respect to the total weight of the composition, preferably ranging from 0.05% to 3% by weight and preferentially ranging from 0.05% to 1% by weight.

The composition according to the invention can additionally comprise an anionic surfactant chosen from alkali metal cetyl phosphate salts. The alkali metal salts are, for example, the sodium salts or the potassium salts. The ionic surfactant is preferably potassium cetyl phosphate.

Use may in particular be made of the monopotassium monocetyl phosphate salt (INCI name: potassium cetyl phosphate) sold under the name "Amphisol K" by DSM Nutritional Products.

This anionic surfactant makes it possible to improve the stability of the composition at high temperature (55° C.) for 2 months.

The anionic surfactant can be present in the composition according to the invention in a content ranging for example from 0.05% to 5% by weight, with respect to the total weight of the composition, preferably ranging from 0.5% to 3% by weight and preferentially ranging from 0.1% to 3% by weight.

The composition according to the invention can comprise a hydrophilic gelling agent which makes it possible to thicken the aqueous phase of the composition.

The hydrophilic gelling agent can be chosen, for example, from:

(i) carboxyvinyl polymers (such as optionally crosslinked acrylic acid polymers), such as the products sold under the Carbopol names (INCI name: Carbomer) by Goodrich;

(ii) polyacrylamides and polymers and copolymers of 2-acrylamido-2-methylpropanesulphonic acid which are optionally crosslinked and/or neutralized, such as the poly(2-acrylamido-2-methylpropanesulphonic acid) sold by Hoechst under the name "Hostacerin AMPS" (INCI name: ammonium polyacryloyldimethyltauratic); crosslinked anionic copolymers of acrylamide and of AMPS which are provided in the form of an emulsion, such as those sold under the name of Sepigel 305 (CTFA name: Polyacryl-amide/$C_{13-14}$ Isoparaffin/Laureth-7) and under the name of Simulgel 600 (CTFA name: Acrylamide/Sodium acryloyldimethyltaurate copolymer/Isohexadecane/Polysorbate 80) by SEPPIC; crosslinked anionic copolymers of acrylic acid and of AMPS which are provided in the form of an emulsion, such as those sold under the name of Simulgel EG (CTFA name: Sodium acrylate/Sodium acryloyldimethyltaurate copolymer/Isohexadecane/Polysorbate 80); 2-acrylamido-2-methylpropanesulphonic acid/ethoxylated $C_{12}$-$C_{14}$ alkyl methacrylate copolymers (Aristoflex LNC from Clariant) or 2-acrylamido-2-methylpropanesulphonic acid/ethoxylated stearyl methacrylate copolymers (Aristoflex HMS and Aristoflex SNC from Clariant);

(iii) polysaccharides, such as xanthan gums, guar gums, alginates or cellulose polymers, such as hydroxyethyl cellulose, hydroxypropyl cellulose or carboxymethyl cellulose;

(iv) inorganic compounds, such as smectites or hectorites which may or may not be modified, such as the Bentone products sold by Rheox, the Laponite products sold by Southern Clay Products or the Veegum HS product sold by R.T. Vanderbilt; and their mixtures. The choice will more particularly be made, among these hydrophilic gelling agents, of the polysaccharides described above, in particular xanthan gum.

The hydrophilic gelling agent can be present in the composition according to the invention in a content ranging for example from 0.01% to 10% by weight, with respect to the total weight of the composition, preferably ranging from 0.1% to 5% by weight and preferentially ranging from 0.1% to 3% by weight.

The composition according to the invention comprises an aqueous phase.

The composition can comprise water in a content ranging for example from 20% to 95% by weight, with respect to the total weight of the composition, preferably ranging from 30% to 90% by weight and preferentially ranging from 40% to 70% by weight.

The water can be a floral water, such as cornflower water, and/or a mineral water, such as water from Vittel, water from Lucas or water from La Roche-Posay, and/or a thermal water.

The composition can additionally comprise an organic solvent which is miscible with water at ambient temperature (25° C.) and which is chosen in particular from monoalcohols having from 2 to 6 carbon atoms, such as ethanol or isopropanol;

polyols having in particular from 2 to 20 carbon atoms, preferably having from 2 to 10 carbon atoms and preferentially having from 2 to 6 carbon atoms, such as glycerol, propylene glycol, butylene glycol, pentylene glycol, hexylene glycol, dipropylene glycol or diethylene glycol;

glycol ethers (having in particular from 3 to 16 carbon atoms), such as mono-, di- or tripropylene glycol ($C_1$-$C_4$)alkyl ethers or mono-, di- or triethylene glycol ($C_1$-$C_4$)alkyl ethers; and their mixtures.

The composition according to the invention can comprise an organic solvent which is miscible with water at ambient temperature, in particular a polyol, in a content ranging for example from 1% to 20% by weight, with respect to the total weight of the composition, preferably ranging from 3% to 15% by weight.

Advantageously, the composition according to the invention has a pH ranging from 3.0 to 8.0, preferably ranging from 4.0 to 8.0, preferentially ranging from 5.0 to 7.0 and more preferentially ranging from 5.5 to 6.5.

The emulsion according to the invention also comprises an oily phase.

Mention may be made, as oils which can more particularly be used in the composition of the invention, for example, of:
  hydrocarbon oils of animal origin, such as perhydrosqualene (or squalane);
  synthetic esters and ethers, in particular of fatty acids, such as oils of formulae $R^1COOR^2$ and $R^1OR^2$ in which $R^1$ represents the residue of a fatty acid comprising from 8 to 29 carbon atoms and $R^2$ represents a linear or branched hydrocarbon chain comprising from 3 to 30 carbon atoms, such as, for example, purcellin oil, isononyl isononanoate, isopropyl myristate, 2-ethylhexyl palmitate, 2-octyldodecyl stearate, 2-octyldodecyl erucate or isostearyl isostearate; hydroxylated esters, such as isostearyl lactate, octyl hydroxystearate, octyldodecyl hydroxystearate, diisostearyl malate, triisocetyl citrate or heptanoates, octanoates or decanoates of fatty alcohols; polyol esters, such as propylene glycol dioctanoate, neopentyl glycol diheptanoate and diethylene glycol diisononanoate; pentaerythritol esters, such as pentaerythrityl tetraisostearate; or lipophilic derivatives of amino acids, such as Isopropyl lauroyl sarcosinate (INCI name), sold under the name Eldew SL 205 by Ajinomoto;
  linear or branched hydrocarbons of mineral or synthetic origin, such as mineral oils (mixture of hydrocarbon oils derived from oil; INCI name: Mineral oil), volatile or nonvolatile liquid paraffins and their derivatives, liquid petrolatum, polydecenes, isohexadecane, isododecane or hydrogenated isoparaffin, such as Parleam® oil, sold by NOF Corporation (INCI name: Hydrogenated polyisobutene);
  silicone oils, such as volatile or nonvolatile poly-methylsiloxanes (PDMS) comprising a linear or cyclic silicone chain which are liquid or pasty at ambient temperature, in particular cyclopolydimethylsiloxanes (cyclomethicones), such as cyclopentasiloxane and cyclohexadimethylsiloxane; polydimethylsiloxanes comprising pendant alkyl, alkoxy or phenyl groups or alkyl, alkoxy or phenyl groups at the end of the silicone chain, which groups have from 2 to 24 carbon atoms; or phenylated silicones, such as phenyl trimethicones, phenyl dimethicones, phenyl(trimethylsiloxy)diphenylsiloxanes, diphenyl dimethicones, diphenyl(methyldiphenyl)trisiloxanes, (2-phenylethyl)trimethylsiloxysilicates and polymethylphenylsiloxanes;
  fluorinated oils, such as those which partially comprise hydrocarbon and/or silicone, such as those described in the document JP-A-2-295912;
  ethers, such as Dicaprylyl ether (CTFA name); and benzoates of $C_{12}$-$C_{15}$ fatty alcohols (Finsolv TN from Finetex);
  their mixtures.

The oil can be present in the composition according to the invention in a content ranging for example from 1% to 50% by weight, with respect to the total weight of the composition, preferably ranging from 5% to 40% by weight and preferentially ranging from 5% to 30% by weight.

The oily phase of the emulsion can comprise other fatty substances, such as waxes; gums, such as silicone gums (dimethiconol); silicone resins, and their mixtures.

The composition according to the invention can comprise at least one organic photoprotective agent which is active in the UV-A and/or UV-B regions (absorbers) and which is soluble in water or fatty substances or else insoluble in the cosmetic solvents commonly used.

As the composition according to the invention exhibits good stability, it is suitable for the formulation of organic UV screening agents: the UV screening agents incorporated in the composition are not decomposed in the presence of ascorbic acid compound.

The organic screening agents are chosen in particular from anthranilates; cinnamic derivatives; dibenzoyl-methane derivatives; ascorbic derivatives; camphor derivatives; triazine derivatives, such as those described in Patent Applications U.S. Pat. No. 4,367,390, EP 863 145, EP 517 104, EP 570 838, EP 796 851, EP 775 698, EP 878 469, EP 933 376, EP 507 691, EP 507 692, EP 790 243 and EP 944 624; benzophenone derivatives; β,β-diphenylacrylate derivatives; benzotriazole derivatives; benzalmalonate derivatives; benz-imidazole derivatives; imidazolines; bis-benzoxazolyl derivatives, such as described in Patents EP 669 323 and U.S. Pat. No. 2,463,264; p-aminobenzoic acid (PABA) derivatives; methylenebis(hydroxyphenylbenzotriazole) derivatives, such as described in Applications U.S. Pat. No. 5,237,071, U.S. Pat. No. 5,166,355, GB 2 303 549, DE 197 26 184 and EP 893 119; screening polymers and screening silicones, such as those described in particular in Application WO 93/04665; dimers derived from α-alkylstyrene, such as those described in Patent Application DE 19 855 649; 4,4-diarylbutadienes, such as described in Applications EP 0 967 200, DE 19 746 654, DE 19 755 649, EP-A-1 008 586, EP 1 133 980 and EP 133 981, and their mixtures.

Advantageously, use is made of a nonionic organic protective screening agent.

The photoprotective agent can be present in the composition according to the invention in a content ranging for example from 0.01% to 30% by weight, with respect to the total weight of the composition, preferably ranging from 0.1% to 25% by weight and preferentially ranging from 0.1% to 20% by weight.

The composition according to the invention can additionally comprise fillers.

The term "fillers" should be understood as meaning colourless or white and inorganic or organic particles of any shape which are insoluble in the medium of the composition, whatever the temperature at which the composition is manufactured, and which do not colour the composition.

The fillers can be of any shape, platelet, spherical or oblong, whatever the crystallographic form (for example, sheet, cubic, hexagonal, orthorhombic, and the like). Mention may be made of: talc, mica, silica, kaolin, powders formed of poly-p-alanine and polyethylene, powders formed of tetrafluoroethylene polymers (Teflon®), lauroyllysine, starch, boron nitride, hollow polymeric microspheres, such as those of poly(vinylidene chloride)/acrylonitrile, such as Expancel® (Nobel Industrie), or of acrylic acid copolymers, silicone resin microbeads (Tospearls® from Toshiba, for example), polyorganosiloxane elastomer particles, precipitated calcium carbonate, magnesium carbonate, basic magnesium carbonate, hydroxyapatite, barium sulphate, aluminium oxides, polyurethane powders, composite fillers, hollow silica microspheres and glass or ceramic microcapsules.

The fillers can be present in the composition in a content ranging for example from 0.1% to 15% by weight, preferably ranging from 0.1% to 10% by weight and preferentially ranging from 0.1% to 5% by weight, with respect to the total weight of the composition.

The composition according to the invention can additionally comprise an active agent chosen from desquamating agents, capable of acting either by promoting exfoliation or on the enzymes involved in the desquamation or decomposition of the corneodesmosomes, moisturizing agents, depigmenting or propigmenting agents, antiglycation agents, NO-synthase inhibitors, 5α-reductase inhibitors, lysyl and/or prolyl hydroxylase inhibitors, agents which stimulate the synthesis of dermal or epidermal macromolecules and/or which prevent their decomposition, agents which stimulate the proliferation of fibroblasts or keratinocytes and/or the differentiation of keratinocytes, muscle relaxants, antimicrobial agents, tightening agents, agents for combating pollution or free radicals, anti-inflammatories, lipolytic active principles or active principles having a favourable activity, direct or indirect, on the reduction in adipose tissue, agents which act on the microcirculation and agents which act on the energy metabolism of the cells.

The emulsion according to the invention can advantageously have a viscosity, measured at 25° C., at a shear rate of 200 $min^{-1}$ (200 revolutions per minute, i.e. a frequency of 50 Hz), ranging from 1 to 4 Pas (10 to 40 poises) and preferably ranging from 2 to 3.5 Pas (20 to 35 poises). The viscosity is measured at 25° C. with a Rheomat 180 viscometer from Mettler equipped with a No. 3 spindle, the measurement being taken after rotating the spindle for 10 minutes (time at the end of which the viscosity and the rotational speed of the spindle are observed to stabilize), at a shear rate of 200 $min^{-1}$.

The composition according to the invention is intended in particular for a topical use, in particular a cosmetic or dermatological topical use.

In a known way, the cosmetic or dermatological composition of the invention can also comprise adjuvants usual in the cosmetic or dermatological field, such as preservatives, fragrances, bactericides, odour absorbers, colouring materials, salts, surfactants, thickeners or bases. The amounts of these various adjuvants are those conventionally used in the field under consideration, for example from 0.01 to 20% of the total weight of the composition. These adjuvants, depending on their nature, can be introduced into the fatty phase or into the aqueous phase.

The composition according to the invention can be applied to the skin, non-scalp hair, eyelashes, hair, nails or lips, according to the use for which it is intended. It can thus be used in a method for the cosmetic treatment of the skin comprising the application of the composition according to the invention to the skin, for example for the purpose of toning it up, of regenerating it or of smoothing out its wrinkles and/or for combating ageing of the skin or the damaging effects of UV radiation and/or for strengthening skin tissues against attacks from the surroundings.

In an alternative form, the composition according to the invention can be used for the manufacture of a dermatological preparation.

The composition can be a care composition, in particular can be a product for caring for the skin, such as a care base for the skin, a care cream (day cream, night cream, antiwrinkle cream) or a makeup base; a care composition for the lips (lip balm); or a sun-protection or self-tanning composition.

The composition can also be a makeup composition, in particular a composition for making up the skin, lips, eyelashes, eyebrows or hair. In particular, the makeup composition can be a foundation, a blusher, an eyeshadow, a concealer or a product for making up the body.

Advantageously, the composition is a leave-in composition.

The emulsion according to the invention can be prepared according to the following general procedure:

The constituents of the aqueous phase are mixed by heating at a temperature of approximately 70° C. The oils and the surfactants are furthermore mixed by heating at a temperature of approximately 80° C. The fatty phase is run into the aqueous phase at a temperature of approximately 70° C. and then the mixture is stirred for 10 minutes at high speed using a turbine mixer. The emulsion obtained is cooled to approximately 60° C. The thickeners are subsequently added and then the mixture is again stirred for 10 minutes. It is cooled to approximately 50° C. The ascorbic acid or derivative, mixed beforehand with water, is subsequently introduced, optionally followed by the other active principles.

The invention will now be illustrated using the following nonlimiting examples.

Comparative Example 1

A composition for caring for the face in the form of an oil-in-water emulsion according to the invention was prepared (Example 1) which has the following composition:

| | |
|---|---|
| Mixture of glyceryl monostearate and of polyethylene glycol (100 EO) stearate (Arlacel 165 FL from Croda) | 2.5 g |
| PEG (20 EO) stearate (Myrj 49 P from Uniqema) | 1 g |
| Stearyl alcohol | 1 g |
| Stearic acid | 3 g |
| Apricot kernel oil | 5 g |

-continued

| | |
|---|---|
| Liquid fraction of shea butter | 6 g |
| Cyclohexasiloxane | 5 g |
| Pentaerythrityl tetrapentanoate | 5 g |
| Isohexadecane | 3 g |
| Beeswax | 0.75 g |
| Silicone wax (Dow Corning 2501 Cosmetic Wax) | 1 g |
| Mixture of dimethiconol and of dimethicone (Dow Corning 1503 Fluid) | 1.5 g |
| Magnesium ascorbyl phosphate | 0.5 g |
| Glycosyl ascorbic acid | 1 g |
| Triethanolamine | 0.85 g |
| Acrylamide/sodium 2-acrylamido-2-methyl-propanesulphonate copolymer as an inverse emulsion at 40% in isohexadecane/water (Simulgel 600 from SEPPIC) | 1.4 g |
| Fillers | 3.1 g |
| Pearlescent agent | 0.5 g |
| Adenosine | 0.1 g |
| Potassium cetyl phosphate | 1.5 g |
| EO-PO-EO block copolymer (Synperonic ® PE/F 108 from Croda) | 0.2 g |
| Glycerol | 8 g |
| Preservatives | q.s. |
| Water | q.s. for 100 g |

A similar composition but not comprising EO-PO-EO block copolymer (Synperonic® PE/F108 from Croda) and potassium cetyl phosphate (Composition 1', not forming part of the invention) was also prepared (amounts deleted replaced by the same weight of water).

The emulsion of Example 1 has good stability after 24 hours at 55° C. and also after 2 months at 45° C. When observed under a microscope, the emulsion obtained is fine and dense.

The composition is applied to the face for daily use during the day.

The comparative emulsion of Example 1' is unstable after storing at 45° C. for 2 months: the emulsion, observed under a microscope, is coarser and more degraded. Phase separation is observed with the naked eye with release at the surface of the oily phase.

Comparative Example 2

A composition for caring for the face in the form of an oil-in-water emulsion according to the invention was prepared (Example 2) which has the following composition:

| | |
|---|---|
| Mixture of glyceryl monostearate and of polyethylene glycol (100 EO) stearate (Arlacel 165 FL from Croda) | 2.5 g |
| PEG (20 EO) stearate (Myrj 49 P from Uniqema) | 1 g |
| Stearyl alcohol | 1 g |
| Stearic acid | 3 g |
| Apricot kernel oil | 7.5 g |
| Rice bran oil | 4.5 g |
| Beeswax | 1.7 g |
| Cyclohexasiloxane | 7 g |
| Mixture of crosslinked polydimethylsiloxane and of polydimethylsiloxane (6 cSt) (24/76) (KSG 16 from Shin Etsu) | 2 g |
| Magnesium ascorbyl phosphate | 0.5 g |
| Glycosyl ascorbic acid | 1 g |
| Triethanolamine | 0.80 g |
| Acrylamide/sodium 2-acrylamido-2-methyl-propanesulphonate copolymer as an inverse emulsion at 40% in isohexadecane/water (Simulgel 600 from SEPPIC) | 1.3 g |
| Fillers | 3.1 g |
| Pearlescent agent | 0.5 g |

-continued

| | |
|---|---|
| Adenosine | 0.1 g |
| Potassium cetyl phosphate | 1.5 g |
| EO-PO-EO block copolymer (Synperonic ® PE/F 108 from Croda) | 0.2 g |
| Glycerol | 5 g |
| Butylene glycol | 2 g |
| Preservatives | q.s. |
| Water | q.s. for 100 g |

A similar composition but not comprising EO-PO-EO block copolymer (Synperonic® PE/F108 from Croda) and potassium cetyl phosphate (Composition 2', not forming part of the invention) was also prepared (amounts deleted replaced by the same weight of water).

The emulsion of Example 2 has good stability after 24 hours at 55° C. and also after 2 months at 45° C. When observed under a microscope, the emulsion obtained is fine and dense.

The composition is applied to the face for daily use during the day.

The comparative emulsion of Example 2' is unstable after storing for 2 months at 45° C.: the emulsion, observed under a microscope, is coarser and more degraded. Phase separation is observed with the naked eye, with release at the surface of the oily phase.

Example 3

A composition for caring for the face in the form of an oil-in-water emulsion was prepared which has the following composition:

| | |
|---|---|
| Glyceryl stearate | 2 g |
| Polyethylene glycol (40 EO) stearate (Myrj 52 P from Croda) | 2.5 g |
| Sorbitan tristearate (Span 65 V from Croda) | 0.9 g |
| Cetyl alcohol | 4.4 g |
| Apricot kernel oil | 5 g |
| Liquid petrolatum | 2.5 g |
| Beeswax | 0.75 g |
| Cyclohexasiloxane | 9 g |
| α,ω-Dihydroxyl polydimethylsiloxane/cyclo-pentadimethylsiloxane (14.7/85.3) mixture (Dow Corning 1501 FL from Dow Corning) | 4 g |
| Magnesium ascorbyl phosphate | 0.5 g |
| Glycosyl ascorbic acid | 2 g |
| Triethanolamine | 1.20 g |
| Fillers | 3 g |
| Adenosine | 0.1 g |
| Tocopherol | 0.2 g |
| Potassium cetyl phosphate | 1.5 g |
| EO-PO-EO block copolymer (Synperonic ® PE/F 108 from Croda) | 0.2 g |
| Glycerol | 5 g |
| Preservatives | q.s. |
| Water | q.s. for 100 g |

The emulsion obtained has good stability after 24 hours at 55° C. and also after 2 months at 45° C. When observed under a microscope, the emulsion obtained is fine and dense.

The composition is applied to the face for daily use during the day.

Comparative Example 4

A composition for caring for the face in the form of an oil-in-water emulsion was prepared which has the following composition:

| | |
|---|---|
| Glyceryl stearate | 2 g |
| Polyethylene glycol (40 EO) stearate (Myrj 52 P from Croda) | 1.2 g |
| Sorbitan tristearate (Span 65 V from Croda) | 0.9 g |
| Cetyl alcohol | 4.4 g |
| Apricot kernel oil | 5 g |
| Liquid petrolatum | 2.5 g |
| Beeswax | 0.75 g |
| Cyclohexasiloxane | 9 g |
| α,ω-Dihydroxyl polydimethylsiloxane/cyclo-pentadimethylsiloxane (14.7/85.3) mixture (Dow Corning 1501 FL from Dow Corning) | 4 g |
| Magnesium ascorbyl phosphate | 0.5 g |
| Glycosyl ascorbic acid | 2 g |
| Triethanolamine | 1.20 g |
| Maize starch | 3 g |
| Adenosine | 0.1 g |
| Tocopherol | 0.2 g |
| Potassium cetyl phosphate | 1.5 g |
| EO-PO-EO block copolymer (Synperonic ® PE/F 108 from Croda) | 0.4 g |
| Glycerol | 5 g |
| 1,2-Octanediol | 0.3 g |
| Preservatives | q.s. |
| Water | q.s. for 100 g |

A similar composition but not comprising EO-PO-EO block copolymer (Synperonic® PE/F108 from Croda) (Composition 4', not forming part of the invention) was also prepared (amount deleted replaced by the same weight of water).

The emulsion of Example 4 has good stability after 24 hours at 55° C. When observed under a microscope, the emulsion obtained is fine and dense.

The composition is applied to the face for daily use during the day.

The comparative emulsion of Example 4' is unstable after storing for 24 hours at 55° C.: the emulsion, observed under a microscope, is coarser and more degraded. Release of oil at the surface is observed with the naked eye.

Example 5

A composition for caring for the face in the form of an oil-in-water emulsion was prepared which has the following composition:

| | |
|---|---|
| Mixture of glyceryl monostearate and of polyethylene glycol (100 EO) stearate (Arlacel 165 FL from Croda) | 2 g |
| PEG (20 EO) stearate (Myrj 49 P from Uniqema) | 0.8 g |
| Stearyl alcohol | 1 g |
| Mixture of glyceryl mono- and distearate (36/64) | 3 g |
| Stearic acid | 3 g |
| 4-tert-Butyl-4'-methoxydibenzoylmethane | 3 g |
| 2-Ethylhexyl 2-cyano-3,3-diphenylacrylate | 7 g |
| 2-Ethylhexyl salicylate | 5 g |
| Octyldodecanol | 3 g |
| Cyclopentasiloxane | 10 g |
| Beeswax | 1 g |
| Myristyl myristate | 2 g |
| 5-(n-Octanoyl)salicylic acid | 0.3 g |
| Triethanolamine | 0.46 g |
| Poly(acrylamidomethylpropanesulphonic acid) partially neutralized with ammonia and highly crosslinked (Hostacerin AMPS from Clariant) | 1.3 g |
| Fillers | 3.2 g |
| Pearlescent agent | 1 g |
| Adenosine | 0.1 g |
| Aqueous soybean protein dispersion with an AM content of 7% | 5 g |
| Potassium cetyl phosphate | 1.5 g |
| EO-PO-EO block copolymer (Synperonic ® PE/F 108 from Croda) | 0.2 g |
| Glycerol | 7 g |
| Preservatives | q.s. |
| Water | q.s. for 100 g |

This emulsion has good stability after 24 hours at 55° C. and also after 2 months at 45° C. When observed under a microscope, the emulsion obtained is fine and dense.

The composition is applied to the face for daily use during the day.

Comparative Example 6

A similar composition to that of Example 1 but not comprising EO-PO-EO block copolymer (Synperonic® PE/F 108 from Croda) and potassium cetyl phosphate (composition not forming part of the invention) was prepared.

The composition obtained is unstable after storing for 2 months at 45° C.: the emulsion, observed under a microscope, is coarser and more degraded. Phase separation with release at the surface of the oily phase is observed with the naked eye.

Comparative Example 7

A composition for caring for the face in the form of an oil-in-water emulsion was prepared which has the following composition:

| | |
|---|---|
| Mixture of glyceryl monostearate and of polyethylene glycol (100 EO) stearate (Arlacel 165 FL from Croda) | 2 g |
| PEG (20 EO) stearate (Myrj 49 P from Uniqema) | 0.8 g |
| Stearyl alcohol | 1 g |
| Stearic acid | 3 g |
| Disodium salt of ethylenediaminetetra-acetic acid | 0.1 g |
| 4-tert-Butyl-4'-methoxydibenzoylmethane | 3 g |
| 2-Ethylhexyl 2-cyano-3,3-diphenylacrylate | 7 g |
| 2-Ethylhexyl salicylate | 5 g |
| Octyldodecanol | 3 g |
| Cyclopentasiloxane | 10 g |
| Beeswax | 1 g |
| Myristyl myristate | 2 g |
| 5-(n-Octanoyl)salicylic acid | 0.3 g |
| Triethanolamine | 0.46 g |
| Poly(acrylamidomethylpropanesulphonic acid) partially neutralized with ammonia and highly crosslinked (Hostacerin AMPS from Clariant) | 1.3 g |
| Fillers | 3.2 g |
| Pearlescent agent | 1 g |
| Adenosine | 0.1 g |
| Aqueous soybean protein dispersion with an AM content of 7% | 5 g |
| EO-PO-EO block copolymer (Synperonic ® PE/F 108 from Croda) | 0.2 g |
| Glycerol | 7 g |
| Preservatives | q.s. |
| Water | q.s. for 100 g |

A similar composition but not comprising EO-PO-EO block copolymer (Synperonic® PE/F108 from Croda) (Composition 7' not forming part of the invention) was also prepared (amount deleted replaced by the same weight of water).

The emulsion of Example 7 has good stability after 24 hours at 55° C. When observed under a microscope, the emulsion obtained is fine and dense.

The composition is applied to the face for daily use during the day.

The comparative emulsion of Example 7' is unstable after storing for 24 hours at 55° C.: the emulsion, observed under a microscope, is coarser and more degraded. Release of oil at the surface is observed with the naked eye.

The above written description of the invention provides a manner and process of making and using it such that any person skilled in this art is enabled to make and use the same, this enablement being provided in particular for the subject matter of the appended claims, which make up a part of the original description and including a composition in the form of an oil-in-water emulsion comprising:

an ester of fatty acid and of polyethylene glycol;
an additional surfactant chosen from esters of $C_{16}$-$C_{22}$ fatty acid and of sorbitan and esters of $C_{16}$-$C_{22}$ fatty acid and of glycerol;
a polycondensate of ethylene oxide and of propylene oxide consisting of polyethylene glycol and polypropylene glycol blocks;
an active principle chosen from ascorbic acid and its salts, glycosyl ascorbic acid, salicylic acid and salicylic acid derivatives of formula (I):

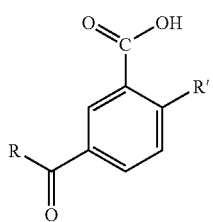

(I)

in which:
the R radical denotes a saturated, linear, branched or cyclic, aliphatic chain having from 2 to 22 carbon atoms; an unsaturated chain having from 2 to 22 carbon atoms comprising one or more double bonds which can be conjugated; an aromatic nucleus bonded to the carbonyl radical directly or via saturated or unsaturated aliphatic chains having from 2 to 7 carbon atoms; it being possible for the said groups to be substituted by one or more identical or different substituents chosen from (a) halogen atoms, (b) the trifluoromethyl group, (c) hydroxyl groups in the free form or in the form esterified by an acid having from 1 to 6 carbon atoms or (d) a carboxyl functional group in the free form or in the form esterified by a lower alcohol having from 1 to 6 carbon atoms;
R' is a hydroxyl group;
and their salts resulting from interaction with an inorganic or organic base.

As used herein, the phrases "selected from the group consisting of," "chosen from," and the like include mixtures of the specified materials. Terms such as "contain(s)" and the like as used herein are open terms meaning 'including at least' unless otherwise specifically noted. Phrases such as "mention may be made," etc. preface examples of materials that can be used and do not limit the invention to the specific materials, etc., listed.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A composition in the form of an oil-in-water emulsion comprising:
an ester of fatty acid and polyethylene glycol;
an additional surfactant selected from the group consisting of an ester of $C_{16}$-$C_{22}$ fatty acid and sorbitan and an ester of $C_{16}$-$C_{22}$ fatty acid and of glycerol;
from 0.01 to 1% by weight, based on the total weight of the composition, of a polycondensate of ethylene oxide and of propylene oxide consisting of polyethylene glycol and polypropylene glycol blocks; and
an active principle selected from the group consisting of ascorbic acid and its salts, glycosyl ascorbic acid, salicylic acid and a salicylic acid compound of formula (I):

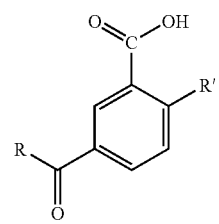

(I)

in which:
the R radical denotes a saturated, linear, branched or cyclic, aliphatic chain having from 2 to 22 carbon atoms; an unsaturated chain having from 2 to 22 carbon atoms comprising one or more double bonds which can be conjugated; an aromatic nucleus bonded to the carbonyl radical directly or via saturated or unsaturated aliphatic chains having from 2 to 7 carbon atoms; wherein R is optionally substituted by one or more identical or different substituents selected from the group consisting of (a) a halogen atom, (b) a trifluoromethyl group, (c) a hydroxyl group in the free form or esterified by an acid having from 1 to 6 carbon atoms and (d) a carboxyl functional group in the free form or esterified by a lower alcohol having from 1 to 6 carbon atoms;
R' is a hydroxyl group;
and their salts resulting from interaction with an inorganic or organic base.

2. The composition according to claim 1, wherein the active principle is selected from the group consisting of magnesium ascorbyl phosphate, glycosyl ascorbic acid and their mixture.

3. The composition according to claim 1, wherein the active principle is at least one selected from the group consisting of salicylic acid and 5-(n-octanoyl)salicylic acid.

4. The composition according to claim 1, wherein the active principle is present in a content ranging from 0.05% to 10% by weight, with respect to the total weight of the composition.

5. The composition according to claim 1, wherein the ester of fatty acid and polyethylene glycol is selected from the group consisting of $C_{16}$-$C_{22}$ fatty acid esters comprising from 8 to 100 ethylene oxide units.

6. The composition according to claim 1, wherein the ester of fatty acid and polyethylene glycol is a polyethylene glycol stearates.

7. The composition according to claim 1, wherein the ester of fatty acid and polyethylene glycol comprises from 20 to 40 ethylene oxide units.

8. The composition according to claim 1, wherein the composition comprises an ester of $C_{16}$-$C_{22}$ fatty acid and sorbitan and the ester is a sorbitan stearate.

9. The composition according to claim 1, wherein the composition comprises an ester of $C_{16}$-$C_{22}$ fatty acid and glycerol and the ester is a glycerol stearate.

10. The composition according to claim 1, wherein the composition comprises a mixture of glyceryl stearate and of polyethylene glycol 100 EO monostearate.

11. The composition according to claim 1, wherein the composition comprises a polyethylene glycol/polypropylene glycol/polyethylene glycol triblock polycondensate.

12. The composition according to claim 1, wherein the polycondensate of ethylene oxide and propylene oxide has a weight-average molecular weight ranging from 1,000 to 15,000.

13. The composition according to claim 1, wherein the composition further comprises a polysaccharide hydrophilic gelling agent.

14. The composition according to claim 1, wherein the composition further comprises at least one cosmetic or dermatological adjuvant selected from the group consisting of a UV screening agent, a filler, a preservative, a fragrance, a bactericide, an odour absorber, a colouring material, a salt, a surfactant, a thickener and a base.

15. The composition of claim 1, wherein the composition comprises from 0.05 to 1% by weight, based on the total weight of the composition, of a polycondensate of ethylene oxide and of propylene oxide consisting of polyethylene glycol and polypropylene glycol blocks.

16. The composition of claim 1, wherein the composition is stable for 24 hours at 55° C.

17. The composition of claim 1, wherein the composition is stable for 2 months at 45° C.

18. The composition of claim 15, wherein the composition is stable for 24 hours at 55° C.

19. The composition of claim 15, wherein the composition is stable for 2 months at 45° C.

* * * * *

UNITED STATES PATENT AND TRADEMARK OFFICE
CERTIFICATE OF CORRECTION

| | | |
|---|---|---|
| PATENT NO. | : 8,980,234 B2 | Page 1 of 1 |
| APPLICATION NO. | : 12/400178 | |
| DATED | : March 17, 2015 | |
| INVENTOR(S) | : Monello | |

It is certified that error appears in the above-identified patent and that said Letters Patent is hereby corrected as shown below:

On the title page item [57], line 13, before "hours" insert --24--.

Signed and Sealed this
Third Day of November, 2015

Michelle K. Lee
*Director of the United States Patent and Trademark Office*